United States Patent
Shiraki et al.

(10) Patent No.: US 8,721,859 B2
(45) Date of Patent: May 13, 2014

(54) ANALYSIS APPARATUS AND ANALYSIS METHOD

(75) Inventors: Yasunori Shiraki, Kyoto (JP); Daisuke Matsumoto, Kyoto (JP); Yusuke Nakayama, Kyoto (JP); Genki Adachi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 27 days.

(21) Appl. No.: 13/427,037

(22) Filed: Mar. 22, 2012

(65) Prior Publication Data

US 2012/0241322 A1 Sep. 27, 2012

(30) Foreign Application Priority Data

Mar. 23, 2011 (JP) ................................. 2011-064411
Feb. 29, 2012 (JP) ................................. 2012-043555

(51) Int. Cl.
*G01N 27/447* (2006.01)
*B01D 57/02* (2006.01)
*C07K 1/26* (2006.01)
*G01N 27/403* (2006.01)

(52) U.S. Cl.
USPC .... 204/452; 422/68.1; 422/82.01; 435/287.1; 204/603

(58) Field of Classification Search
USPC ................. 204/450–458, 600–620; 422/68.1, 422/82.01; 435/287.1
See application file for complete search history.

(56) References Cited

U.S. PATENT DOCUMENTS

2003/0136552 A1* 7/2003 Beebe et al. ................... 165/140
2006/0062696 A1* 3/2006 Chow et al. .................... 422/100
2006/0210994 A1* 9/2006 Joyce ................................. 435/6
2009/0045057 A1* 2/2009 Hattori ........................... 204/450
2010/0108514 A1* 5/2010 Seto et al. ...................... 204/454
2010/0137163 A1* 6/2010 Link et al. ........................ 506/16
2011/0005932 A1* 1/2011 Jovanovich et al. .......... 204/453
2011/0226339 A1* 9/2011 Aoki et al. ........................ 137/1

FOREIGN PATENT DOCUMENTS

| EP | 2418480 A2 | 2/2012 |
| EP | 2434272 A1 | 3/2012 |
| JP | 10-010088 A | 1/1998 |
| JP | 2000-074880 A | 3/2000 |
| JP | 2001-099813 A | 4/2001 |
| JP | 2001-194338 A | 7/2001 |

(Continued)

OTHER PUBLICATIONS

European Search Report issued in corresponding European Patent Application No. 12160935.8 dated Jul. 11, 2012.

*Primary Examiner* — Jennifer Dieterle
(74) *Attorney, Agent, or Firm* — Morgan, Lewis & Bockius LLP

(57) ABSTRACT

An analysis apparatus is an apparatus that performs electrophoresis using a microchip provided with a channel. The analysis apparatus includes a cooling unit (an electron cooling element and a driving circuit) that cools the microchip, a voltage application unit (electrodes and a power supply circuit) that applies voltage to a buffer solution filled in the channel of the microchip, an optical analysis unit (a light source, a light receiving element, and an analysis unit) that conducts, through the microchip, optical analysis of a sample introduced in the channel, and a control unit that controls the cooling unit, the voltage application unit, and the optical analysis unit. The control unit causes the cooling unit to start cooling the microchip, and after the microchip has been cooled, causes the voltage application unit and the optical analysis unit to operate.

11 Claims, 20 Drawing Sheets

(56) References Cited

FOREIGN PATENT DOCUMENTS

| | | | |
|---|---|---|---|
| JP | 2003-166976 A | | 6/2003 |
| WO | 99/12016 A1 | | 3/1999 |
| WO | WO 99/12016 | * | 3/1999 |
| WO | 2004/059309 A1 | | 7/2004 |
| WO | 2007/063719 A1 | | 6/2007 |
| WO | WO 2009/081722 | * | 7/2009 |
| WO | 2010/141921 A1 | | 12/2010 |
| WO | WO 2010/141921 | * | 12/2010 |

* cited by examiner

Tm : Ambient temperature

T₁(t) : Upper surface temperature of microchip

Ta : Lower surface temperature of microchip

FIG. 9

$$\lambda \frac{\partial T^2}{\partial^2 y} = \rho c \frac{\partial T}{\partial t} \qquad T(y,t)$$

| Initial conditions | t = 0 | $T = T_m$ |
|---|---|---|
| Boundary conditions | t > 0 | $T_{y=0} = T_a$ |
| | | $\lambda \frac{\partial T}{\partial y}\bigg|_{y=Y} = \alpha\{T_m - T_1(t)\}$ |
| | t = ∞ | $T_1(t) = T_2$ |
| | | $\lambda \frac{\partial T}{\partial y}\bigg|_{y=Y} = \lambda \frac{T_2 - T_a}{Y} = \alpha(T_m - T_2)$ |

Tm : Ambient temperature

T2 : Upper surface temperature of microchip

Ta : Lower surface temperature of microchip

FIG. 11

$$\lambda \frac{\partial T^2}{\partial^2 y} = 0 \qquad T(y)$$

| Boundary conditions | $t \geq 0$ | $T_{y=0} = T_a$ |
| --- | --- | --- |
| | | $T_{y=Y} = T_2$ |
| | | $\lambda \frac{\partial T}{\partial y}\bigg|_{y=Y} = \lambda \frac{T_2 - T_a}{Y} = \alpha \{T_m - T_2\}$ |

Tm : Ambient temperature

T3(x, t) : Upper surface temperature of microchip

Tb(t) : Lower surface temperature of microchip

FIG. 13

$$\lambda\left(\frac{\partial T^2}{\partial^2 x}+\frac{\partial T^2}{\partial^2 y}\right)+q=\rho c\frac{\partial T}{\partial t} \quad T(x,y,t) \quad q(x,y,t)$$

| Initial conditions | $t=0$ | $q=0$ |
| --- | --- | --- |
| | | $T_{y=0}=T_a$ |
| | | $T_{y=Y}=T_2$ |

| Boundary conditions | $t<t_3 - t_2$ | $q=0$ |
| --- | --- | --- |
| | | $T_{y=0}=T_b(t)$ |
| | | $\left.\lambda\dfrac{dT}{dy}\right|_{y=Y}=\alpha\{T_m-T_3(x,t)\}$ |
| | | $\lambda\dfrac{dT}{dx}=0$ |

} State 3

| Boundary conditions | $t=t_3 - t_2$ | $q=0$ |
| --- | --- | --- |
| | | $T(b, t_3-t_2)=T_{min}$ |
| | | $T_{y=0}=T_b(t_3-t_2)$ |
| | | $T_{y=Y}=T_3(t_3-t_2)$ |
| | | $\lambda\dfrac{dT}{dx}=0$ |

| Boundary conditions | $t>t_3 - t_2$ | $q_{x=a,y=b}=Q$ |
| --- | --- | --- |
| | | $q_{x\neq a,y\neq b}=0$ |
| | | $T_{y=0}=T_b(t)$ |
| | | $\left.\lambda\dfrac{dT}{dy}\right|_{y=Y}=\alpha\{T_m-T_3(x,t)\}$ |
| | | $\left.\lambda\dfrac{dT}{dx}\right|_{x=0}=0$ |
| | | $\left.\lambda\dfrac{dT}{dx}\right|_{x=X}=0$ |
| | | $T(a,b)<T_{max}$ |
| | $t=\infty$ | $T_{y=0}=T_c$ |

} State 4

Tm : Ambient temperature

T5(x) : Upper surface temperature of microchip

Tc : Lower surface temperature of microchip

FIG. 15

$$\lambda\left(\frac{\partial T^2}{\partial^2 x}+\frac{\partial T^2}{\partial^2 y}\right)+q=0 \quad T(x,y) \quad q(x,y)$$

| Boundary conditions | $t \geq 0$ | $q_{x=a, y=b} = Q$ |
| --- | --- | --- |
| | | $q_{x \neq a, y \neq b} = 0$ |
| | | $\lambda \frac{dT}{dx}\bigg|_{x=0} = 0$ |
| | | $\lambda \frac{dT}{dx}\bigg|_{x=X} = 0$ |
| | | $\lambda \frac{dT}{dx}\bigg|_{x=a} = 0$ |
| | | $T_{y=0} = T_c$ |
| | | $T(a,b) = T_g$ |

ANALYSIS APPARATUS AND ANALYSIS METHOD

CROSS-REFERENCE TO RELATED APPLICATION

This application is based upon and claims the benefit of priority from Japanese patent application Nos. 2011-64411, filed on Mar. 23, 2011, and 2012-43555 filed on Feb. 29, 2012, the disclosures of which are incorporated herein in their entirety by reference.

BACKGROUND OF THE INVENTION

1. Field of the Invention

The present invention relates to an analysis apparatus using electrophoresis and an analysis method.

2. Background Art

Conventionally, electrophoresis is used in the fields of analytical biology and analytical biochemistry. Capillary electrophoresis is known as a representative example of electrophoresis (see, for example, JP 2001-99813A and JP 2003-166976A). In capillary electrophoresis, a capillary (microtubule) filled with a buffer solution is used, and a sample is injected into the capillary. Furthermore, both ends of the capillary are immersed in the buffer solution, and in this condition, a voltage is applied inside the capillary.

Upon application of a voltage, the sample is separated while moving within the capillary. Then, the inside of the capillary is irradiated with, for example, ultraviolet rays, visible light, or infrared rays through a window provided partway along the capillary. Light transmitted through the capillary is received by a light receiving element, and thereafter analysis of the sample is conducted based on the received light, using absorptiometry.

Moreover, in recent years, electrophoresis using microchips in place of capillaries has also been proposed. Microchips are generally made up of a glass substrate provided with fine grooves, and a cover bonded to the glass substrate so as to cover the grooves. With microchips, the formation of grooves in the glass substrate is implemented by applying semiconductor manufacturing technology, and therefore, the width, depth, and number of grooves can be easily set. For this reason, microchips could play a leading role in electrophoresis in future.

Furthermore, in electrophoresis, because the migration speeds of molecules are affected by temperature, the temperature of the buffer solution needs to be managed so as to be kept within the optimal range during voltage application. For this reason, most apparatuses for performing electrophoresis (electrophoresis apparatuses) are provided with a cooling apparatus in order to suppress a temperature rise due to voltage application. Examples of the cooling apparatus that are used include an air blowing device and a Peltier element.

Incidentally, in the case of capillary electrophoresis, since capillaries have low heat capacity, the inside of the capillaries can be easily kept within the optimal temperature range simply by operating a cooling apparatus. However, with microchips, because of their higher heat capacity as compared with capillaries, it is difficult to keep the inside of the microchips within the optimal temperature range simply by arranging and operating a cooling apparatus.

SUMMARY OF THE INVENTION

It is one object of the present invention to resolve the above problems and provide an analysis apparatus and an analysis method that can optimize the temperature of a microchip in electrophoresis using a microchip.

In order to attain the above object, the analysis apparatus according to the present invention is an analysis apparatus that performs electrophoresis using a microchip provided with a channel. The apparatus includes a cooling unit that cools the microchip, a voltage application unit that applies voltage to a buffer solution filled in the channel of the microchip, an optical analysis unit that conducts, through the microchip, optical analysis of a sample introduced in the channel, and a control unit that controls the cooling unit, the voltage application unit, and the optical analysis unit, wherein the control unit causes the cooling unit to start cooling the microchip, and after the microchip has been cooled, causes the voltage application unit and the optical analysis unit to operate.

With the above features, according to the present invention, the microchip is sufficiently cooled in advance before execution of electrophoresis, and electrophoresis is executed thereafter. The present invention enables the temperature of the microchip to be optimized in electrophoresis using a microchip.

With the analysis apparatus of the present invention described above, a mode is possible in which the control unit causes the voltage application unit and the optical analysis unit to operate, after a set period of time has elapsed since the cooling unit was caused to start cooling the microchip. In this mode, the microchip can be reliably cooled.

The analysis apparatus according to the present invention described above is preferably in a mode in which the analysis apparatus further includes a temperature sensor for measuring a temperature of the microchip, wherein if the temperature measured by the temperature sensor is less than or equal to a first set temperature, the control unit causes the voltage application unit and the optical analysis unit to operate. In this mode, the microchip can be more reliably cooled because whether or not cooling is sufficient can be determined based on the temperature of the microchip.

Furthermore, the analysis apparatus according to the present invention described above may be in a mode in which if the temperature measured by the temperature sensor is less than or equal to a second set temperature, the control unit causes the cooling unit to stop cooling or reduce output. If the temperature within the channel of the microchip becomes too low, the viscosity of samples increases and electrophoresis becomes difficult, but such a situation can be avoided in the above mode.

Furthermore, the analysis apparatus according to the present invention described above is also preferably in a mode in which the control unit causes the cooling unit to increase output immediately before causing the voltage application unit and the optical analysis unit to operate, and causes the cooling unit to reduce output after operations of the voltage application unit and the optical analysis unit have ended. In the above mode, a rise in the temperature of the microchip can be more strongly suppressed, and therefore it is easy to respond to an increase in the heating value of the microchip.

Moreover, the analysis apparatus according to the present invention described above is also preferably in a mode in which the analysis apparatus further includes a first stage and a second stage on which the microchip is to be placed, wherein the cooling unit includes a first cooling unit that cools the microchip placed on the first stage, and a second cooling unit that cools the microchip placed on the second stage, the voltage application unit applies voltage to the microchip placed on the second stage, the optical analysis unit conducts optical analysis of the sample on the microchip placed on the second stage, while the microchip is placed on the first stage, the control unit cools the microchip with the first cooling unit, and when the microchip is thereafter placed on the second stage, the control unit executes voltage application by the voltage application unit and optical analysis by the optical analysis unit while cooling the microchip with the second cooling unit. In the above mode, in the case where there are a plurality of microchips to be measured, the microchip to be measured next can be cooled in advance, thus improving the efficiency of measurement.

With the analysis apparatus according to the present invention described above, it is sufficient that the cooling unit is at least one of an air blowing device, an electron cooling element, and a heat pipe.

Furthermore, with the analysis apparatus according to the present invention described above, it is preferable for the microchip to include a main body portion in which the channel is formed, and a heat radiation member provided on a surface of the main body portion, and the heat radiation member is formed from a material having higher thermal conductivity than a material forming the main body portion. In this case, cooling efficiency in the microchip can be improved.

Moreover, with the analysis apparatus of the present invention described above, it is preferable for the microchip to include a main body portion in which the channel is formed, and a second channel for passing a cooling medium is further formed along the channel within the main body portion. In this case, the efficiency of cooling in the microchip can also be improved.

In order to attain the above object, the analysis method according to the present invention is an analysis method for performing an analysis of a sample through electrophoresis using a cooling apparatus, a voltage application apparatus, and an optical analysis apparatus, the cooling apparatus cooling a microchip provided with a channel, the voltage application apparatus applying voltage to a buffer solution filled in the channel of the microchip, and the optical analysis apparatus conducting, through the microchip, optical analysis of the sample that is introduced in the channel, the method comprising the steps of (a) cooling the microchip using the cooling apparatus, and (b) causing the voltage application apparatus and the optical analysis apparatus to operate, after the microchip has been cooled.

The analysis method according to the present invention described above is preferably in a mode in which a temperature sensor for measuring a temperature of the microchip is used, and in the step (b), if the temperature measured by the temperature sensor is less than or equal to a first set temperature, the voltage application apparatus and the optical analysis apparatus are caused to operate. Furthermore, in this mode, it is preferable for the method to further include the step of (c) if the temperature measured by the temperature sensor is less than or equal to a second set temperature, stopping the cooling apparatus from cooling the microchip or reducing output of the cooling apparatus.

Furthermore, with the analysis method according to the present invention described above is preferably in a mode in which in the step (a), output of the cooling apparatus is increased immediately before the voltage application apparatus and the optical analysis apparatus are caused to operate, and in the step (b), the output of the cooling apparatus is reduced after operations of the voltage application apparatus and the optical analysis apparatus have ended.

As described above, with the analysis apparatus and the analysis method according to the present invention, it is possible to optimize the temperature of the microchip in electrophoresis using a microchip.

BRIEF DESCRIPTION OF THE DRAWINGS

FIG. 9 shows equations of state satisfied by a microchip in State 1.

FIG. 11 shows equations of state satisfied by a microchip in State 2.

FIG. 13 shows equations of state satisfied by a microchip in State 3 or State 4.

FIG. 15 shows equations of state satisfied by a microchip in State 5.

DETAILED DESCRIPTION OF EXEMPLARY EMBODIMENT

Embodiment 1

Hereinafter, an analysis apparatus and an analysis method according to Embodiment 1 of the present invention will be described with reference to FIGS. 1 to 4.

Configuration of Analysis Apparatus

Figure 1:
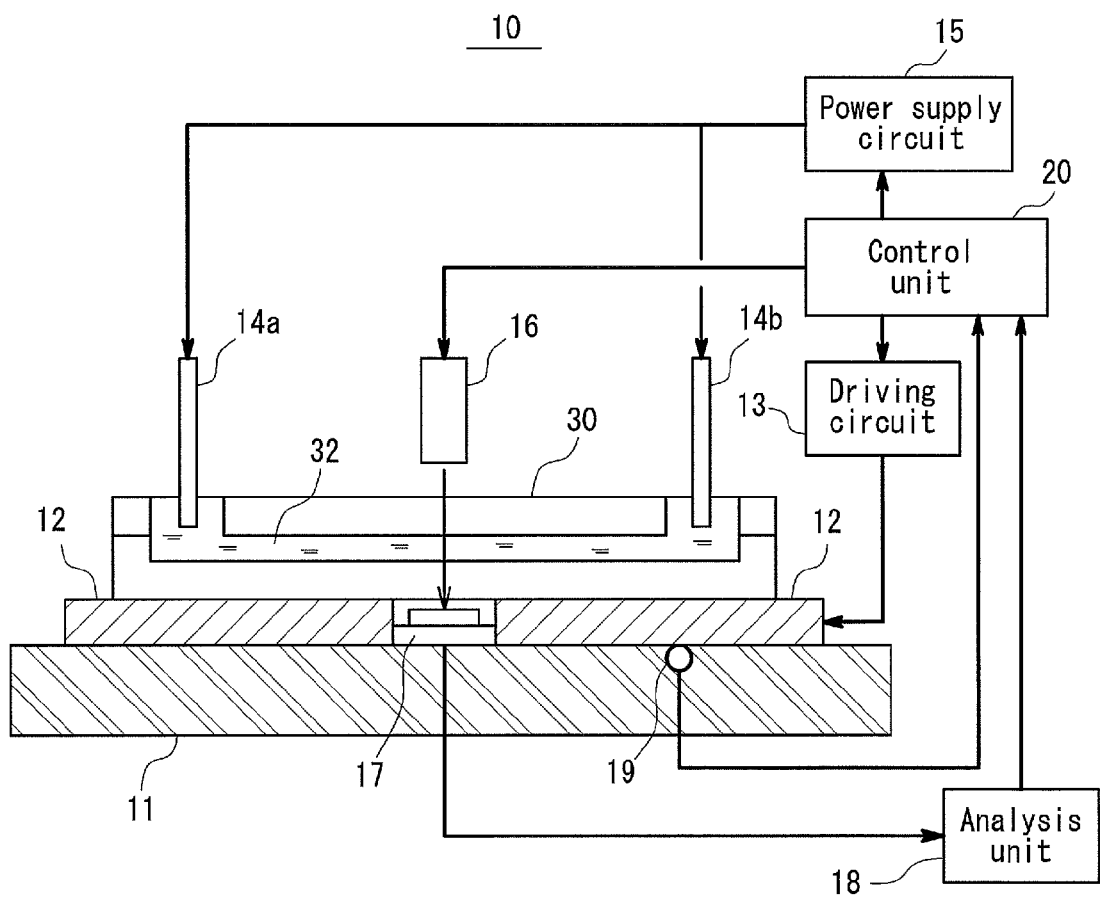
FIG. 1 is a configuration diagram showing the configuration of an analysis apparatus according to Embodiment 1 of the present invention.

First, the configuration of the analysis apparatus 10 according to Embodiment 1 of the present invention will be described with reference to FIG. 1. FIG. 1 is a block diagram showing the configuration of the analysis apparatus according to Embodiment 1 of the present invention. As shown in FIG. 1, the analysis apparatus 10 of Embodiment 1 is an analysis apparatus 10 that performs electrophoresis using a microchip 30. As will be described later, the microchip 30 is provided with a channel 32 in which a buffer solution is filled and furthermore a sample to be analyzed is injected.

As shown in FIG. 1, the analysis apparatus 10 also includes a cooling unit that cools the microchip 30, a voltage application unit that applies voltage to the buffer solution filled in the channel 32, an optical analysis unit that conducts, through the microchip 30, optical analysis of a sample introduced in the channel, and a control unit 20. In Embodiment 1, the analysis apparatus 10 also includes a stage 11 on which the microchip 30 is to be placed.

In Embodiment 1, the cooling unit is a cooling apparatus that includes an electron cooling element 12 disposed between the stage 11 and the microchip 30, and a driving circuit 13 that drives the electron cooling element 12. One specific example of the electron cooling element 12 is a Peltier element. When the driving circuit 13 supplies current to the electron cooling element 12 in accordance with an instruction from the control unit 20, heat absorption by the electron cooling element 12 occurs and the microchip 30 is cooled.

Note that in Embodiment 1, the cooling unit may be an air blowing device or a heat pipe, instead of the electron cooling element 12. Furthermore, in Embodiment 1, a form is possible in which a combination of at least two of the electron cooling element 12, an air blowing device, and a heat pipe is used as the cooling unit.

In Embodiment 1, the voltage application unit is a voltage application apparatus that includes a pair of electrodes 14a and 14b disposed at the respective ends of the channel 32, and a power supply circuit 15 that applies voltage between these electrodes. When the power supply circuit 15 applies voltage between the electrodes 14a and 14b in accordance with an instruction from the control unit 20, electrophoresis occurs within the channel 32. In this case, heat is generated within the channel 32, and the temperature of the microchip 30 rises.

In the present embodiment, the optical analysis unit is an optical analysis apparatus that includes a light source 16 that irradiates the channel 32 of the microchip 30 with light, a light receiving element 17 that receives light transmitted through the channel 32 and outputs a signal in accordance with the amount of the light received, and an analysis unit 18. The light receiving element 17 is disposed on the stage 11 such that its light receiving surface faces the microchip 30. The light source 16 is disposed above the microchip 30 such that its light emitting surface faces the microchip 30 on the stage 11.

The analysis unit 18 measures the component quantity or component ratio of a target component based on the signal output from the light receiving element 17, and outputs the measurement result to the outside. Specifically, in the present embodiment, the analysis unit 18 includes an arithmetic apparatus that executes, for example, absorptiometry based on the signal output from the light receiving element 17 and calculates the component quantity of a target component.

The control unit 20 controls the cooling unit, the voltage application unit, and the optical analysis unit. Specifically, the control unit 20 instructs the driving circuit 13 to supply current, instructs the power supply circuit 15 to apply voltage, and instructs the light source 16 to perform light irradiation.

The control unit 20 also causes the cooling unit to start cooling the microchip 30, and after the microchip 30 has been cooled, causes the voltage application unit and the optical analysis unit to operate. Specifically, when the analysis apparatus 10 is powered on, the control unit 20 first causes the driving circuit 13, which constitutes the cooling unit, to supply current. Then, after the microchip 30 has been sufficiently cooled, the control unit 20 causes the power supply circuit 15 to apply voltage and further causes the light source 16 to perform light irradiation. As a result, the analysis unit 18 executes measurement of the component quantity of a target component through the microchip 30.

Furthermore, in Embodiment 1, whether or not the microchip 30 has been sufficiently cooled is determined by, for example, measuring the temperature of the microchip with a temperature sensor 19, which will be described later. Specifically, if the temperature measured by the temperature sensor 19 is less than or equal to a set temperature (a first set temperature), the microchip 30 is determined as having been sufficiently cooled.

Figure 4:
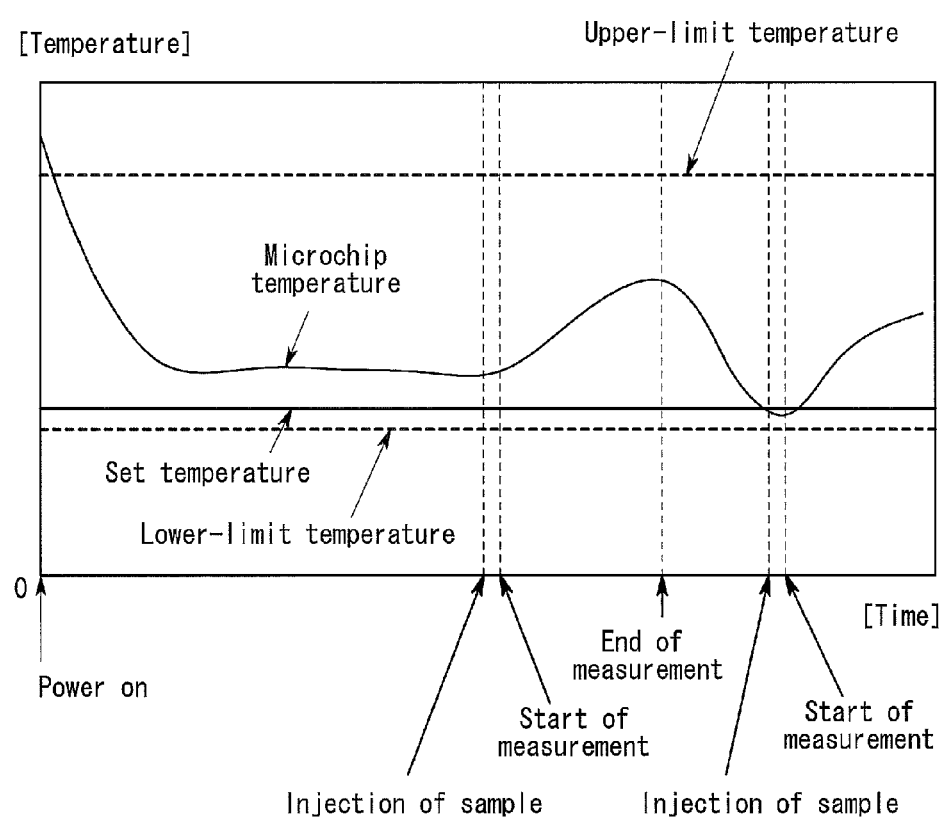
FIG. 4 shows a change in the temperature of a microchip when the analysis apparatus according to Embodiment 1 of the present invention is operated.

In the present embodiment, the analysis apparatus 10 can further include the temperature sensor 19 for measuring the temperature of the microchip 30. References to a "temperature sensor for measuring the temperature of the microchip" in this specification should be understood as a temperature sensor for directly or indirectly measuring the temperature of the microchip. In the case of indirect measurement, the temperature sensor is not located in direct contact with the microchip. In actuality, in the present embodiment, the temperature sensor 19 outputs a signal corresponding to the temperature where it is located, i.e., under the electron cooling element 12. In this case, the control unit 20 determines whether or not the temperature of the microchip 30 is lower than a preset lower limit value (lower-limit temperature: see FIG. 4), based on the signal from the temperature sensor 19, i.e., if the signal output by the temperature sensor 19 corresponds to a temperature below a second set temperature, it is determined that the temperature of the microchip is lower than the lower limit temperature. In FIG. 4, the temperature of the microchip 30 that is shown is measured in a calibration step by another thermometer that is different from the temperature sensor 19. The temperature measured by temperature sensor 19 is not shown in FIG. 4. The upper and lower limit temperatures are not used for comparison with the temperature of the microchip, whereas the first and second set temperatures are used for comparison with the temperature measured by the temperature sensor 19 (the second set temperature is not shown in FIG. 4). If the temperature of the microchip 30 is determined as being lower than the lower-limit temperature, the control unit 20 causes the cooling unit to stop cooling or reduce output. This is because if the temperature within the channel 32 of the microchip 30 becomes too low, the viscosity of samples increases and electrophoresis becomes difficult. It is noted that the first set temperature is set as a temperature higher than the second set temperature.

Figure 2:
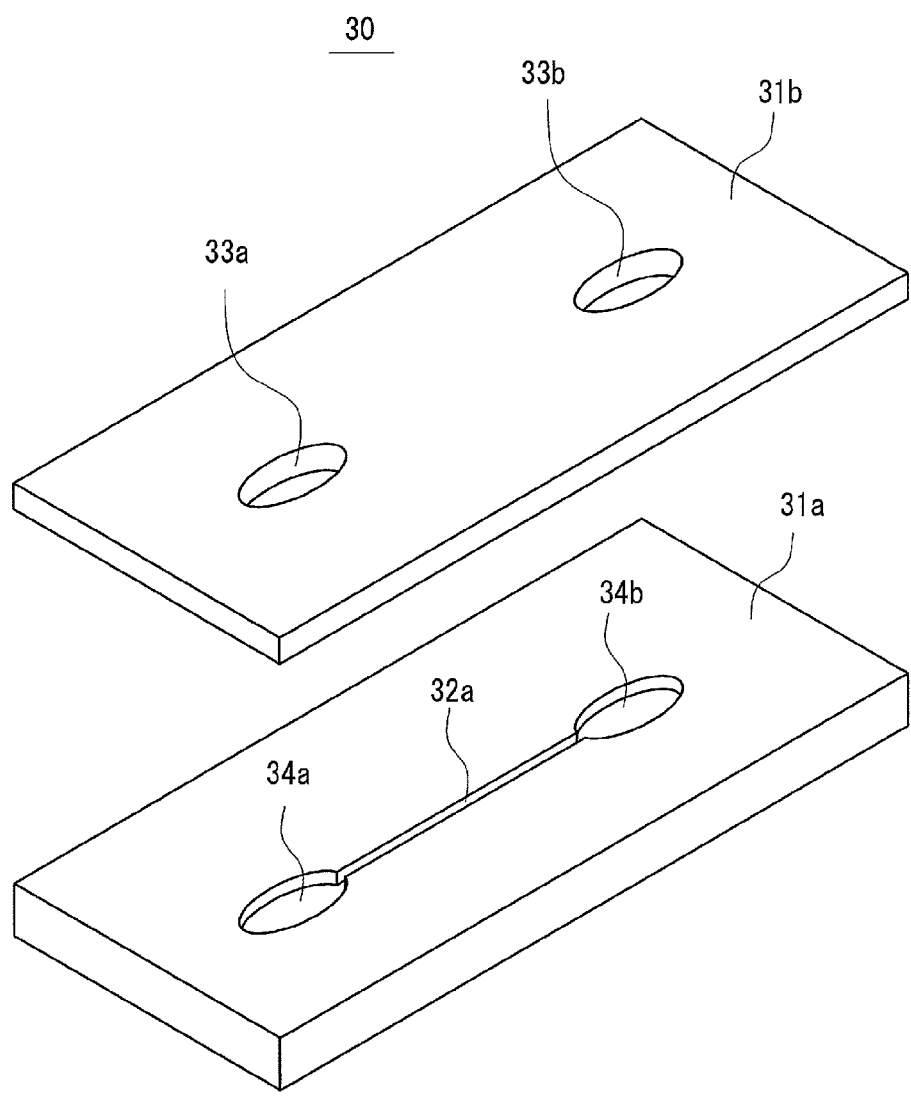
FIG. 2 is an exploded perspective view showing an example of a microchip to be used in Embodiment 1 of the present invention.

Now, the configuration of the microchip 30 used in Embodiment 1 will be described with reference to FIG. 2. FIG. 2 is an exploded perspective view showing an example of the microchip used in Embodiment 1 of the present invention.

As shown in FIG. 2, the microchip 30 includes a substrate 31a and a cover member 31b that covers the substrate 31a. The substrate 31a and the cover member 31b are both formed from a light transmissive material such as a transparent resin material or glass.

The substrate 31a includes a pair of recessed portions 34a and 34b and a groove 32a connecting these recessed portions.

The cover member 31b includes through holes 33a and 33b that are formed at positions aligned with respective openings of the recessed portions 34a and 34b of the substrate 31a overlaid on the cover member 31b.

When the substrate 31a and the cover member 31b are overlaid on each other, the upper surface of the groove 32a is blocked up, thus forming the channel 32 shown in FIG. 1. In this case, a portion formed by aligning the recessed portion 34a and the through hole 33a and a portion formed by aligning the recessed portion 34b and the through hole 33b serve as liquid reservoirs of the buffer solution, in which the electrodes 14a and 14b are disposed respectively.

In the example of FIG. 2, the position at which the light source 16 performs light irradiation and the position at which the light receiving element 17 receives transmitted light are both not particularly limited as long as they face the channel 32. It is, however, to be noted that in terms of irradiation efficiency, it is preferable for the cover member 31b to have a recess in a portion that faces the light source 16. Furthermore, in terms of light receiving efficiency, it is also preferable for the substrate 31a to have a recess in a portion that faces the light receiving element 17.

Moreover, in the case of providing such recesses, it is preferable for the main surface of the microchip 30 to have a film adhering thereto in advance in order to prevent dust or the like from entering these recesses before use. Note that the film adhering to the cover member 31b is preferably formed so as to at the same time cover the through holes 33a and 33b, in addition to the recesses.

Operation of Analysis Apparatus

Figure 3:
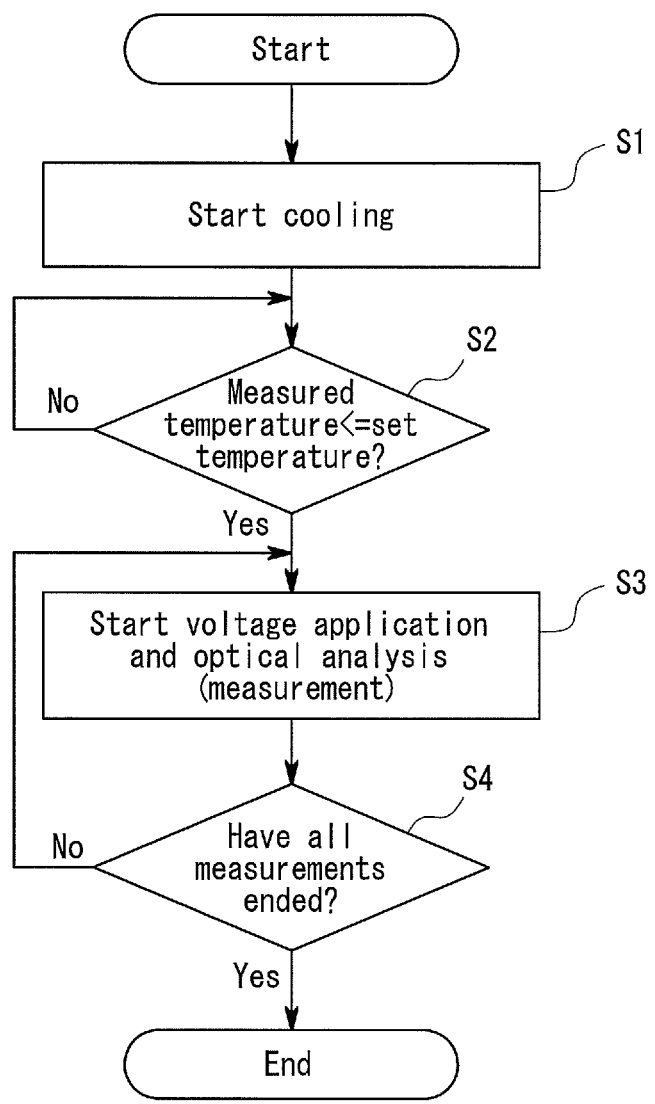
FIG. 3 is a flowchart showing the operation of the analysis apparatus according to Embodiment 1 of the present invention.

Next, the operation of the analysis apparatus 10 according to Embodiment 1 of the present invention will be described with reference to FIGS. 3 and 4. FIG. 3 is a flowchart showing the operation of the analysis apparatus according to Embodiment 1 of the present invention. FIG. 4 shows a change in the temperature of a microchip when the analysis apparatus according to Embodiment 1 of the present invention is operated. Note that FIGS. 1 and 2 are also appropriately referenced in the following description. In Embodiment 1, an analysis method is implemented by operating the analysis apparatus 10. The description of the analysis method according to Embodiment 1 is substituted with the description of the operation of the analysis apparatus 10.

As shown in FIG. 3, when the analysis apparatus 10 is powered on, the control unit 20 first causes the cooling unit to start cooling the microchip 30 (step S1). Specifically, the control unit 20 causes the driving circuit 13 to start supplying current to the electron cooling element 12. In this case, the value of current supplied to the electron cooling element 12 is set constant in order to keep the set temperature constant in the cooling unit. Through the execution of step S1, the temperature of the microchip 30 starts dropping gradually as shown in FIG. 4.

Next, the control unit 20 determines whether or not the temperature measured by the temperature sensor 19 is less than or equal to the set temperature (step S2). As a result of the determination in step S2, if the measured temperature is not less than or equal to the set temperature, the control unit 20 enters its standby state. On the other hand, if the result of the determination in step S2 indicates that the measured temperature is less than or equal to the set temperature, the control unit 20 executes step S3.

In step S3, when a sample is injected into the channel 32 of the microchip 30 by an operator, the control unit 20 causes the voltage application unit to start applying voltage and causes the optical analysis unit to start conducting optical analysis (step S3). Specifically, the control unit 20 causes the power supply circuit 15 to apply voltage between the electrodes 14a and 14b and further causes the light source 16 to perform light irradiation. This increases the temperature of the microchip 30, but the temperature will not exceed the upper-limit temperature because the cooling unit continues to cool the microchip.

When step S3 has been executed, the light receiving element 17 outputs a signal in accordance with the amount of light received, and accordingly the analysis unit 18 measures the component quantity of a target component based on the output signal. When the measurement has ended, the analysis unit 18 notifies the control unit 20 of that fact. Upon receiving the notification, the control unit 20 causes the voltage application unit to stop apply voltage and causes the optical analysis unit to stop conducting optical analysis.

Next, the control unit 20 determines whether or not all measurements have ended (step S4). Specifically, in step S4, the control unit 20 determines whether or not an operator has input an instruction to end all measurements. As a result of the determination in step S4, if all measurements have not ended, the operator will inject a new sample into the microchip 30, upon which the control unit 20 executes step S3 again. On the other hand, if the result of the determination in step S4 indicates that all measurements have ended, the control unit 20 ends the processing.

As described above, in Embodiment 1, the microchip 30 is sufficiently cooled in advance prior to execution of electrophoresis, and electrophoresis is executed thereafter. Accordingly, Embodiment 1 enables the temperature of the microchip 30 to be optimized in electrophoresis using the microchip 30.

Embodiment 2

Next is a description of an analysis apparatus and an analysis method according to Embodiment 2 of the present invention. The analysis apparatus according to Embodiment 2 has a similar configuration to the analysis apparatus 10 of Embodiment 1 shown in FIG. 1, but it differs from the analysis apparatus of Embodiment 1 in the processing performed by the control unit. Note that the microchip 30 shown in FIGS. 1 and 2 is also used in Embodiment 2.

Figure 5:
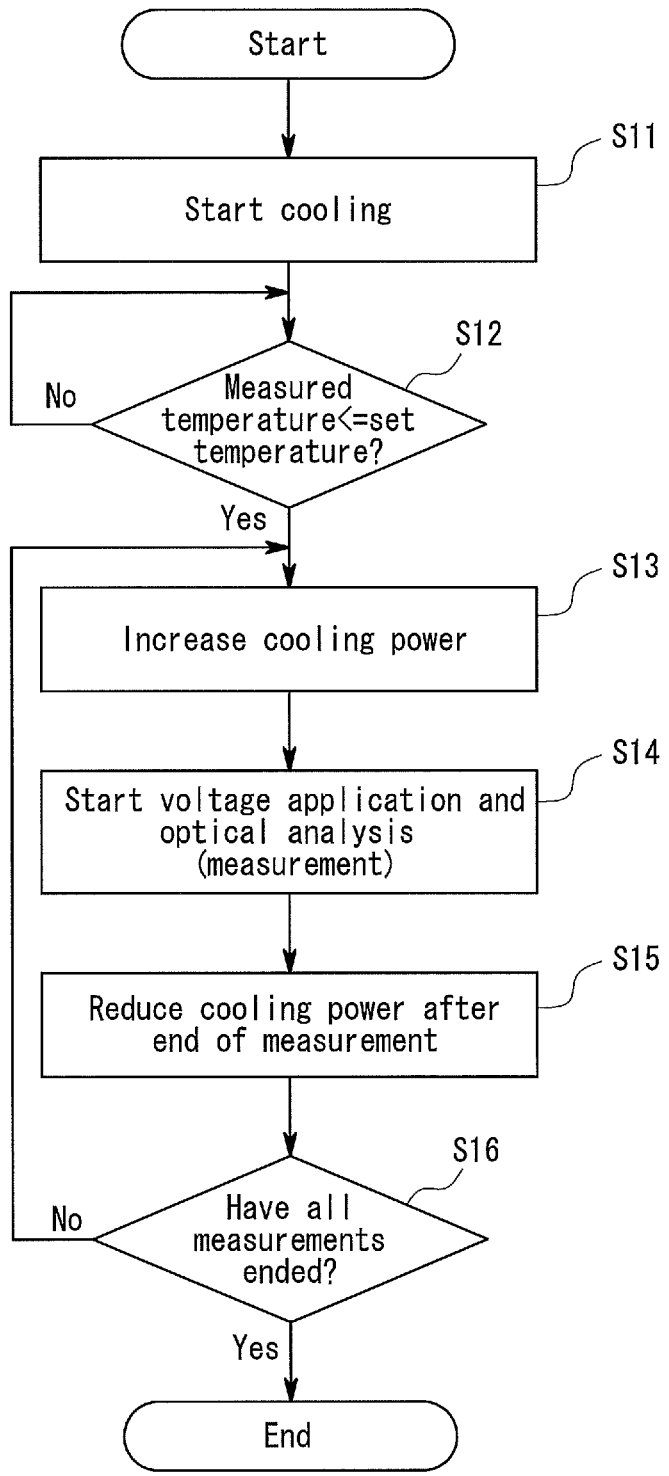
FIG. 5 is a flowchart showing the operation of an analysis apparatus according to Embodiment 2 of the present invention.
Figure 6:
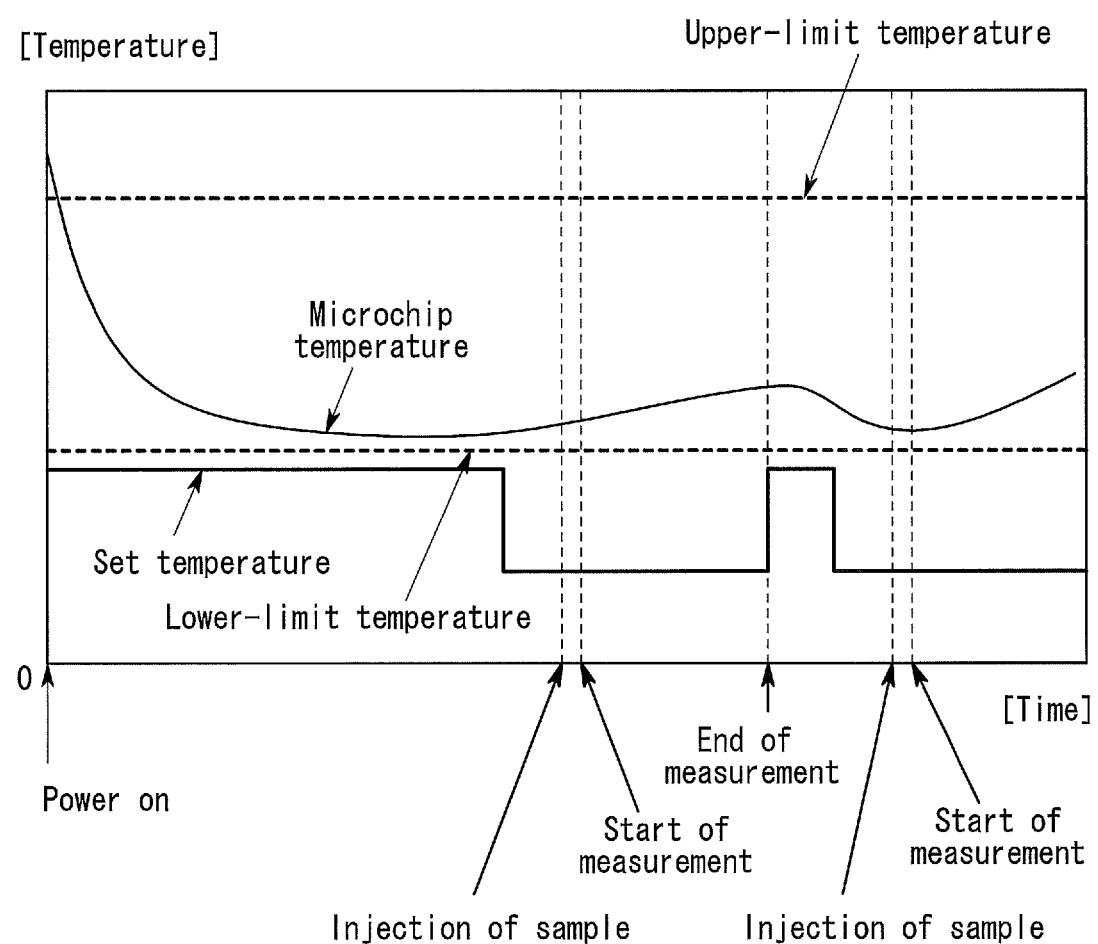
FIG. 6 shows a change in the temperature of a microchip when the analysis apparatus according to Embodiment 2 of the present invention is operated.

The following description focuses on differences from Embodiment 1, with reference to FIGS. 5 and 6. FIG. 5 is a flowchart showing the operation of the analysis apparatus according to Embodiment 2 of the present invention. FIG. 6 shows a change in the temperature of the microchip when the analysis apparatus according to Embodiment 2 of the present invention is operated. Note that FIGS. 1 and 2 are also appropriately referenced in the following description.

As shown in FIG. 5, when the analysis apparatus 10 is powered on, the control unit 20 first causes the cooling unit to start cooling the microchip 30 (step S11). Step S11 is the same as step S1 shown in FIG. 3. In this case, the relationship between the set temperature and the temperature of the microchip is, as shown in FIG. 6, the same as in the case of FIG. 4 described in Embodiment 1.

Next, the control unit 20 determines whether or not the temperature measured by the temperature sensor 19 is less than or equal to the set temperature (step S12). As a result of the determination in step S12, if the measured temperature is not less than or equal to the set temperature, the control unit 20 enters its standby state. On the other hand, if the result of the determination in step S12 indicates that the measured temperature is less than or equal to the set temperature, the control unit 20 executes step S13.

In step S13, the control unit 20 increases output of the cooling unit and thereby enhances cooling. In Embodiment 2, the control unit 20 increases the value of current supplied from the driving circuit 13 to the electron cooling element 12.

Then, when a sample is injected into the channel 32 of the microchip 30 by an operator, the control unit 20 causes the voltage application unit to start applying voltage and causes the optical analysis unit to start conducting optical analysis (step S14). Step S14 is the same as step S3 shown in FIG. 3.

When step S14 has been executed, the light receiving element 17 outputs a signal in accordance with the amount of light received, and accordingly the analysis unit 18 measure the component quantity of a target component based on the output signal. In Embodiment 2, when the measurement has ended, the analysis unit 18 also notifies the control unit 20 of that fact.

Then, when receiving the notification from the analysis unit 18, the control unit 20 stops voltage application by the voltage application unit and optical analysis by the optical analysis unit, and at the same time, reduces output of the cooling unit (step S15). Execution of step S15 suppresses the occurrence of a situation in which the temperature of the microchip 30 becomes lower than the lower-limit temperature.

Then, the control unit 20 determines whether or not all measurements have ended (step S16). Step S16 is the same as step S4 shown in FIG. 3. In step S16, the control unit 20 also determines whether or not an operator has input an instruction to end all measurements. As a result of the determination in step S16, if all measurements have not ended, the operator will inject a new sample into the microchip 30, upon which the control unit 20 executes step S13 again. On the other hand, if the result of the determination in step S16 indicates that all measurements have ended, the control unit 20 ends the processing.

As described above, in Embodiment 2, the control unit 20 increases the output of the cooling unit immediately before operating the voltage application unit and the optical analysis unit (immediately before step S14), and then reduces the output of the cooling unit after operations of the voltage application unit and the optical analysis unit have ended. Thus, according to Embodiment 2, it is possible to suppress a rise in the temperature of the microchip 30 more strongly than in Embodiment 1, as shown in FIG. 6. In recent years, there is a tendency for the channel 32 to have a shorter length and a higher heating value due to demand for downsizing of the microchip 30, and Embodiment 2 is in particular effective in such a case.

Temperature Analysis

Figure 7:
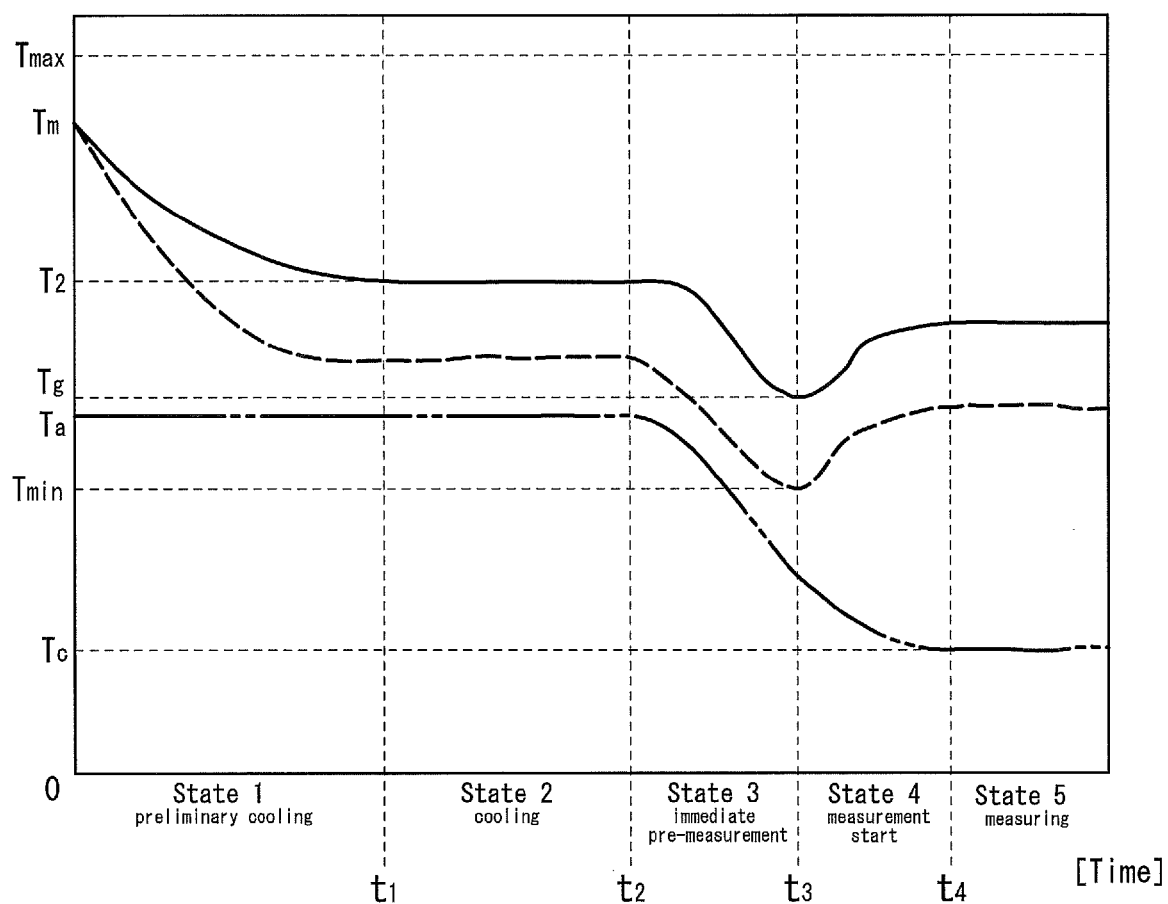
FIG. 7 is a graph showing the upper surface temperature of a microchip, the channel temperature, and the temperature on the stage with the passage of time.

Now, analysis of the temperature of a microchip in the case of using the analysis apparatus and the analysis method according to Embodiment 2 will be described with reference to FIGS. 7 to 15. FIG. 7 is a graph showing the upper surface temperature of the microchip, the channel temperature, and the temperature on the stage with the passage of time.

In the graph shown in FIG. 7, the horizontal axis indicates time t, and the vertical axis indicates temperature T. In FIG. 7, the time interval from the start (t=0) to $t_1$ is defined as State 1 (preliminary cooling), the time interval from $t_1$ to $t_2$ as State 2 (cooling), the time interval from $t_2$ to $t_3$ as State 3 (immediate pre-measurement), the time interval from $t_3$ to $t_4$ as State 4 (measurement start), and the time interval from $t_4$ onward as State 5 (measuring). In State 4 and State 5, electrophoresis occurs within the channel 32 (see FIGS. 1 and 2) of the microchip 30.

As indicated by the graph in FIG. 7 showing changes in the temperature on the stage, the output of the cooling unit is constant from the start (t=0) to $t_2$, is increased at time $t_3$, and is thereafter reduced gradually. The adjustment of the output of the cooling unit needs to be performed based on the upper surface temperature of the microchip and the channel temperature. The following describes an analysis technique to be used at each temperature for each state.

Temperature Analysis: State 1

Figure 8:
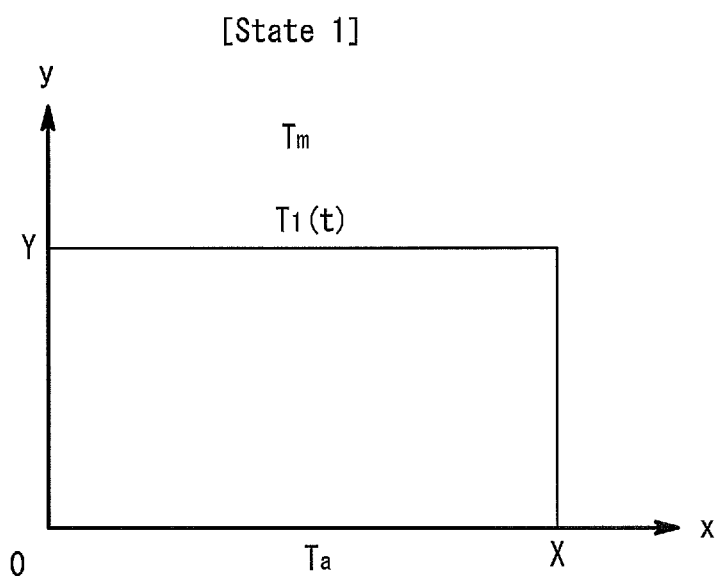
FIG. 8 shows an example in which a microchip in State 1 is modeled.

State 1 is described with reference to FIGS. 8 and 9. FIG. 8 shows an example in which a microchip in State 1 is modeled. In FIG. 8, the microchip 30 is shown in a state as viewed from a widthwise side face (see FIG. 2).

FIG. 9 shows an equation of state satisfied by a microchip in State 1. FIG. 9 also shows equations of state in the case where initial conditions and boundary conditions are given. In FIG. 9, $\lambda$ indicates the thermal conductivity of the microchip 30 (which is unique to the material), and $\alpha$ indicates the heat transfer coefficient from the surface of the microchip to the air (which depends on the material and the ambient conditions).

In the respective equations in FIG. 9, there are the following preconditions: the diameter (or width) of the channel 32 is extremely small as compared with the dimensions of the microchip 30 so that the channel 32 can be regarded as a point, the thickness of the microchip 30 is so small that heat radiation from the side face of the microchip 30 can be ignored, and it is accordingly assumed that there is no temperature distribution in the x-axis direction (only the temperature distribution in the y-axis direction in FIG. 8 is taken into consideration). Note that State 1 is a non-steady state.

If the microchip 30 shown in FIG. 2 is used as the microchip, the temperature of the microchip 30 in State 1 can be simulated by applying an analytical technique such as a difference method or a finite-element method to the equations shown in FIG. 9. As a result, the output of the cooling unit can be set to an appropriate value in State 1.

Temperature Analysis: State 2

Figure 10:
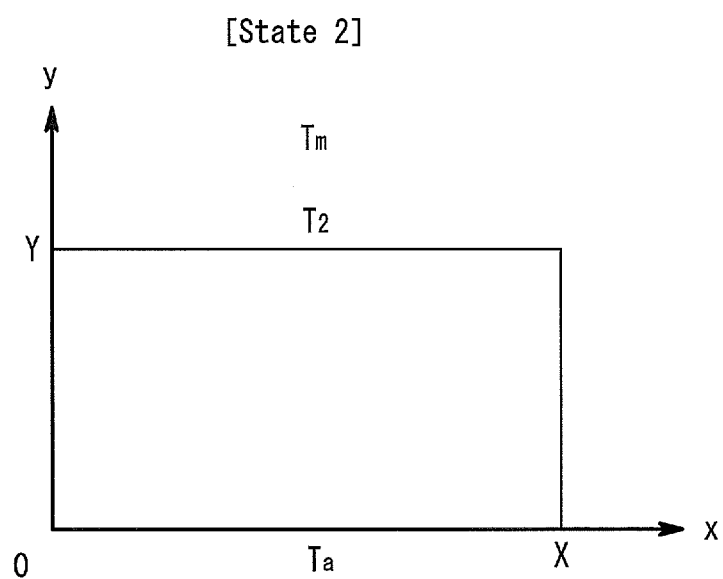
FIG. 10 shows an example in which a microchip in State 2 is modeled.

State 2 is described with reference to FIGS. 10 and 11. FIG. 10 shows an example in which a microchip in State 2 is modeled. In FIG. 10, the microchip 30 is also shown in a state as viewed from a widthwise side face (see FIG. 2).

FIG. 11 shows an equation of state satisfied by a microchip in State 2. FIG. 11 also shows equations of state in the case where boundary conditions are given. In FIG. 11, $\lambda$ similarly indicates the thermal conductivity of the microchip 30 (which is unique to the material), and $\alpha$ similarly indicates the heat transfer coefficient from the surface of the microchip to the air (which depends on the material and the ambient conditions).

Furthermore, in the respective equations in FIG. 11, there are also the following preconditions: the diameter (or width) of the channel 32 is extremely small as compared with the dimensions of the microchip 30 so that the channel 32 can be regarded as a point, the thickness of the microchip 30 is so small that heat radiation from the side face of the microchip 30 can be ignored, and it is accordingly assumed that there is no temperature distribution in the x-axis direction (only the temperature distribution in the y-axis direction in FIG. 10 is taken into consideration). Note that State 2 is a steady state.

If the microchip 30 shown in FIG. 2 is used as the microchip, the temperature of the microchip 30 in State 2 can be simulated by applying an analytical technique such as a difference method or a finite-element method to the equations shown in FIG. 11. As a result, the output of the cooling unit can be set to an appropriate value in State 2.

Temperature Analysis: State 3 and State 4

Figure 12:
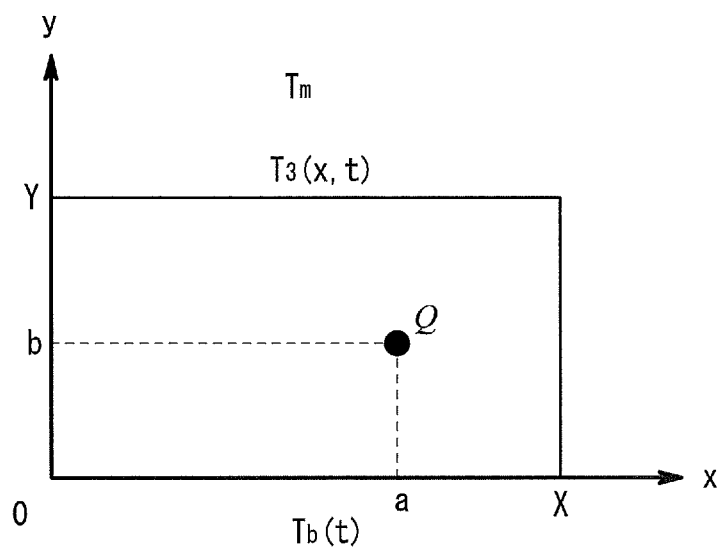
FIG. 12 shows an example in which a microchip in State 3 and State 4 is modeled.

State 3 and State 4 are described with reference to FIGS. 12 and 13. FIG. 12 shows an example in which a microchip in State 3 and State 4 is modeled. In FIG. 12, the microchip 30 is also shown in a state as viewed from a widthwise side face (see FIG. 2).

FIG. 13 shows an equation of state satisfied by a microchip in State 3 or State 4. FIG. 13 also shows equations of state in the case where initial conditions and boundary conditions are given. In FIG. 13, λ similarly indicates the thermal conductivity of the microchip 30 (which is unique to the material), and α similarly indicates the heat transfer coefficient from the surface of the microchip to the air (which depends on the material and the ambient conditions).

Furthermore, in the respective equations in FIG. 13, there are the following preconditions: the diameter (or width) of the channel 32 is extremely small as compared with the dimensions of the microchip 30 so that the channel 32 can be regarded as a point, and the thickness of the microchip 30 is so small that heat radiation from the side face of the microchip 30 can be ignored. Moreover, in State 3 or State 4, heat is generated from the channel and therefore temperature distribution also occurs in the x-axis direction. For this reason, State 3 and State 4 can be considered to be two-dimensional non-steady states.

If the microchip 30 shown in FIG. 2 is used as the microchip, the temperature of the microchip 30 in State 3 and State 4 can be simulated by applying an analytical technique such as a difference method or a finite-element method to the equations shown in FIG. 13. As a result, the output of the cooling unit can be set to an appropriate value in State 3 and State 4.

Temperature Analysis: State 5

Figure 14:
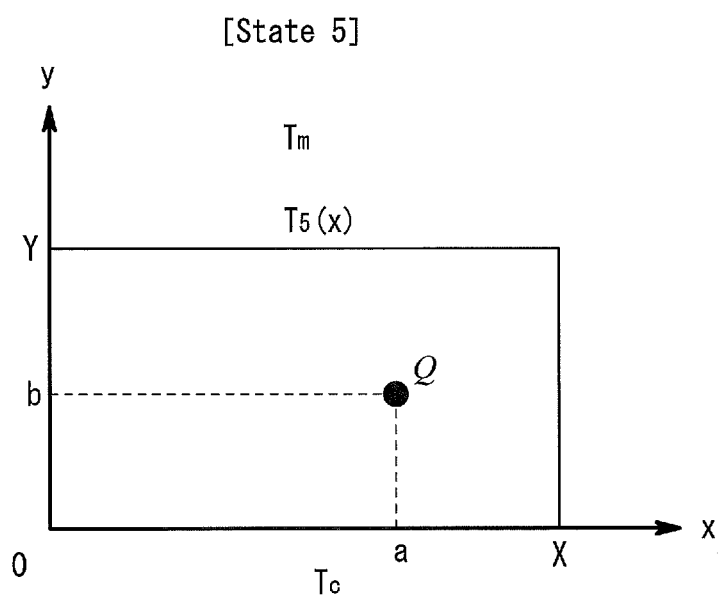
FIG. 14 shows an example in which a microchip in State 5 is modeled.

State 5 is described with reference to FIGS. 14 and 15. FIG. 14 shows an example in which a microchip in State 5 is modeled. In FIG. 14, the microchip 30 is also shown in a state as viewed from a widthwise side face (see FIG. 2).

FIG. 15 shows an equation of state satisfied by a microchip in State 5. FIG. 15 also shows equations of state in the case where boundary conditions are given. In FIG. 15, λ similarly indicates the thermal conductivity of the microchip 30 (which is unique to the material).

Furthermore, in the respective equations in FIG. 15, there are the following preconditions: the diameter (or width) of the channel 32 is extremely small as compared with the dimensions of the microchip 30 so that the channel 32 can be regarded as a point, and the thickness of the microchip 30 is so small that heat radiation from the side face of the microchip 30 can be ignored. Moreover, in State 5, heat is generated from the channel, and therefore temperature distribution also occurs in the X-axis direction. For this reason, it can be thought that State 5 is a two-dimensional non-steady state.

If the microchip 30 shown in FIG. 2 is used as the microchip, the temperature of the microchip 30 in State 5 can be simulated by applying an analytical technique such as a difference method or a finite-element method to the equations shown in FIG. 15. As a result, the output of the cooling unit can be set to an appropriate value in State 5.

Note that if the microchip is other than the microchip 30 shown in FIG. 2, the aforementioned equations of state (FIGS. 9, 11, 13, and 15) need to be changed in consideration of the shape, material, and dimensions of the microchip.

Furthermore, Embodiments 1 and 2 described above are not limited to the examples described above, and may be in any form including any of Modifications 1 to 3 described below.

Modification 1

Figure 16:
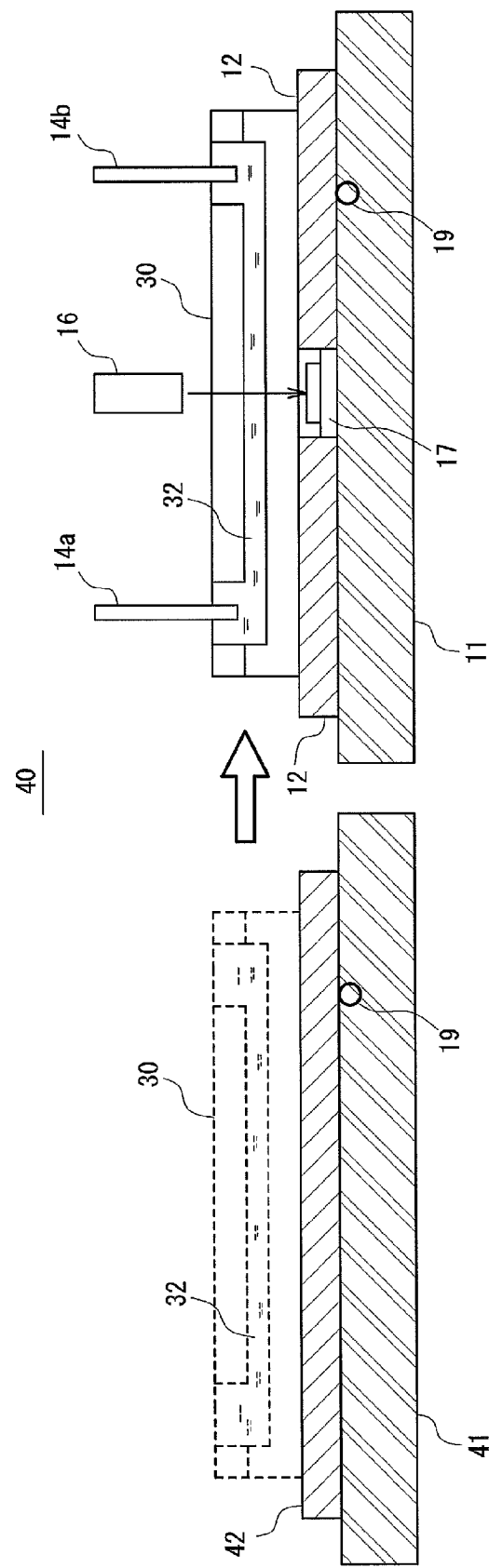
FIG. 16 shows the configuration of an analysis apparatus according to Modification 1.

Modification 1 that can be made to Embodiments 1 and 2 is described with reference to FIG. 16. FIG. 16 shows the configuration of an analysis apparatus according to Modification 1. As shown in FIG. 16, an analysis apparatus 40 according to Modification 1 further includes a stage 41 and an electron cooling element 42, in addition to the configuration of the analysis apparatus 10 shown in FIG. 1. Note that the driving circuit 13, the power supply circuit 15, the analysis unit 18, and the control unit 20 shown in FIG. 1 are not shown in FIG. 16.

With this configuration, while the microchip 30 is placed on the stage 41, the control unit 20 causes the driving circuit 13 (see FIG. 1) to supply current to the electron cooling element 42 so as to cool the microchip 30 on the stage 41.

Then, when the microchip 30 is moved from the stage 41 to the stage 11 and placed on the stage 11, the control unit 20 enables voltage application and optical analysis to be executed while cooling the microchip 30. In other words, the control unit 20 instructs the driving circuit 13 (see FIG. 1) to supply current to the electron cooling element 12, instructs the power supply circuit 15 to apply voltage between the electrodes 14a and 14b, and instructs the light source 16 to perform light irradiation.

As described above, according to Modification 1, the cooling of the microchip 30 prior to the start of measurement is performed on the stage 41, whereas the measurement and the cooling at the time of the measurement are performed on the stage 11. With Modification 1, in the case where there are a plurality of microchips 30 to be measured, the microchip to be measured next can be cooled in advance, thus improving the efficiency of the measurement.

Modification 2

Figure 17A:
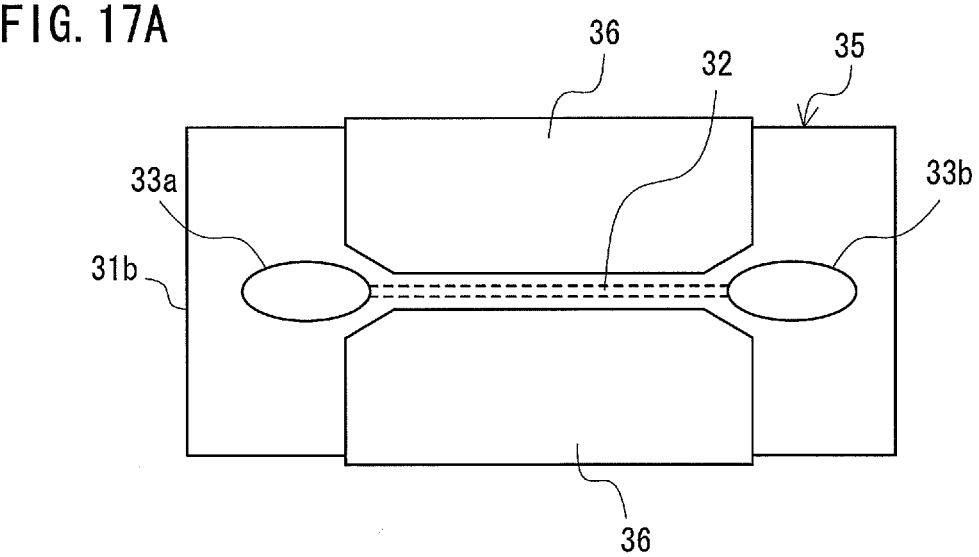
FIG. 17 show an example of the configuration of a microchip according to Modification 2, FIG. 17A being a plan view, FIG. 17B being a bottom view, and FIG. 17C being a side view.
Figure 17B:
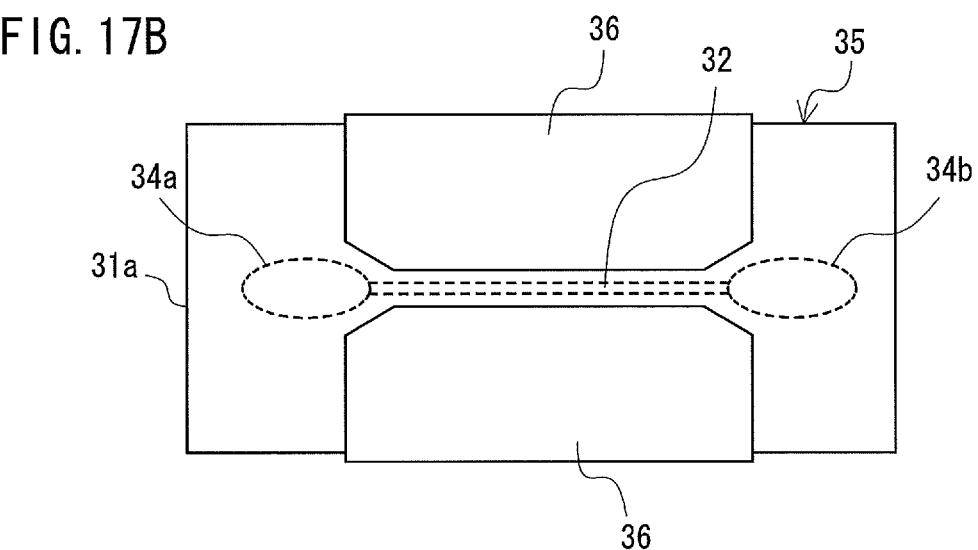
Figure 17C:
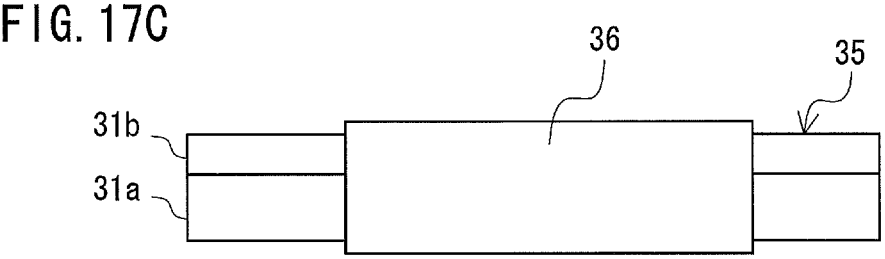

Modification 2 that can be made to Embodiments 1 and 2 is described with reference to FIGS. 17 to 19. FIG. 17 show an example of the configuration of a microchip according to Modification 2, FIG. 17A being a plan view, FIG. 17B being a bottom view, and FIG. 17C being a side view FIG. 18 show another example of the configuration of the microchip according to Modification 2, FIG. 18A being a plan view, FIG. 18B being a bottom view, and FIG. 18C being a side view FIG. 19 show sill another example of the configuration of the microchip according to Modification 2, FIG. 19A being a plan view of a cover member and FIG. 19B being a plan view of a substrate.

In Modification 2, a microchip that has a superior heat radiation property than the microchip 30 shown in FIG. 2 is used as the microchip. In the example shown in FIGS. 17A to 17C, like the microchip 30 shown in FIG. 2, a microchip 35 includes a substrate 31a and a cover member 31b that covers the substrate 31a, and the microchip 35 also includes a heat radiation member 36. The heat radiation member 36 is formed from a material such as a metal material that has higher thermal conductivity than the material forming the main body portion (the substrate 31a and the cover member 31b) of the microchip.

Furthermore, as shown in FIGS. 17A and 17B, the heat radiation member 36 is formed such that the light irradiation from the light source 16 (see FIG. 1) to the channel 32 and the reception of transmitted light by the light receiving element 17 (see FIG. 1) are not inhibited. Specifically, the heat radiation member 36 is formed so as to not shield the channel 32 on the main surface. The heat radiation member 36 is also formed so as to avoid the vicinity of the through holes 33a and 33b provided in the cover member 31b, in order to avoid contact with the electrodes 14a and 14b (see FIG. 1).

Figure 18A:
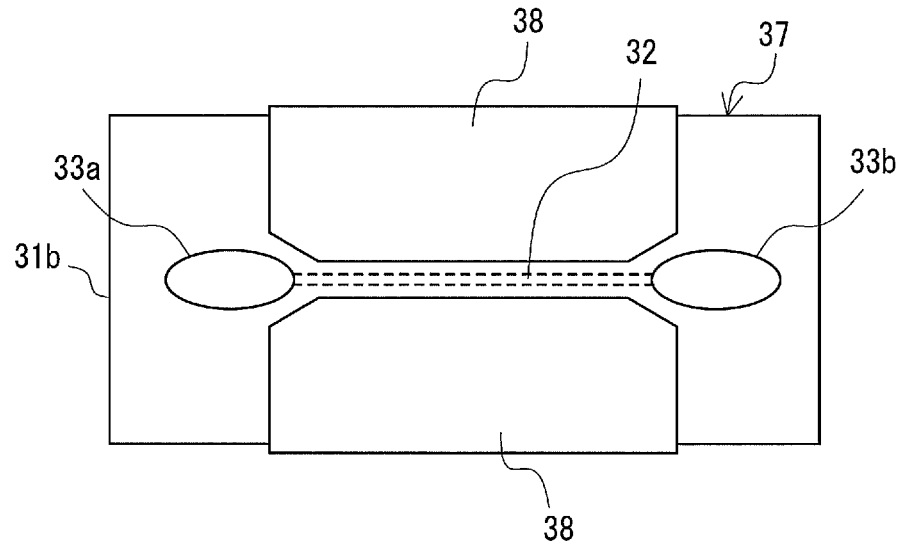
FIG. 18 show another example of the configuration of the microchip according to Modification 2, FIG. 18A being a plan view, FIG. 18B being a bottom view, and FIG. 18C being a side view.
Figure 18B:
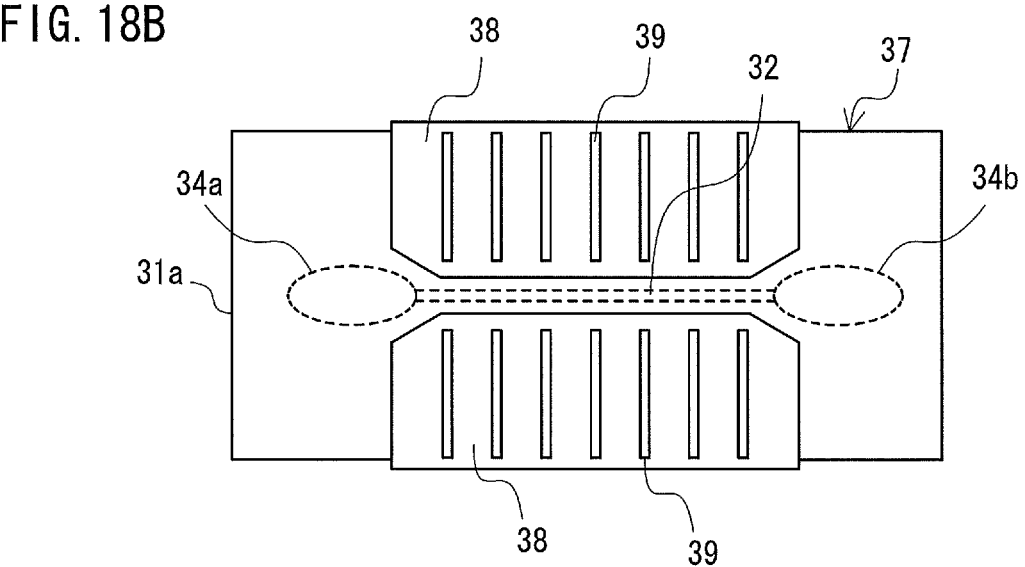
Figure 18C:
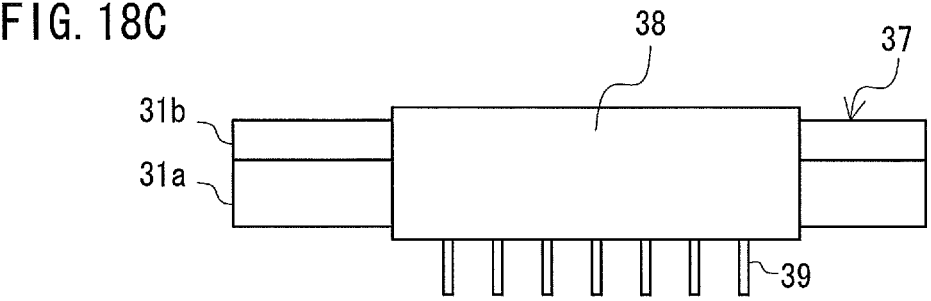
Figure 19A:
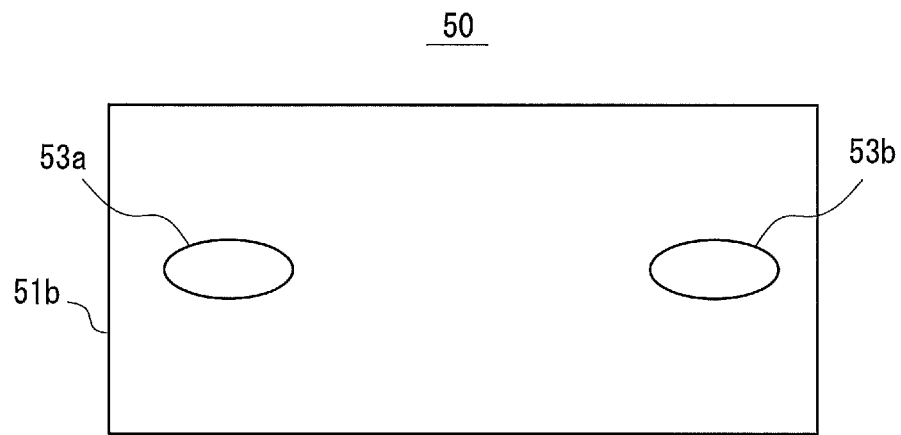
FIG. 19 show another example of the configuration of the microchip according to Modification 2, FIG. 19A being a plan view of a cover member and FIG. 19B being a plan view of a substrate.
Figure 19B:
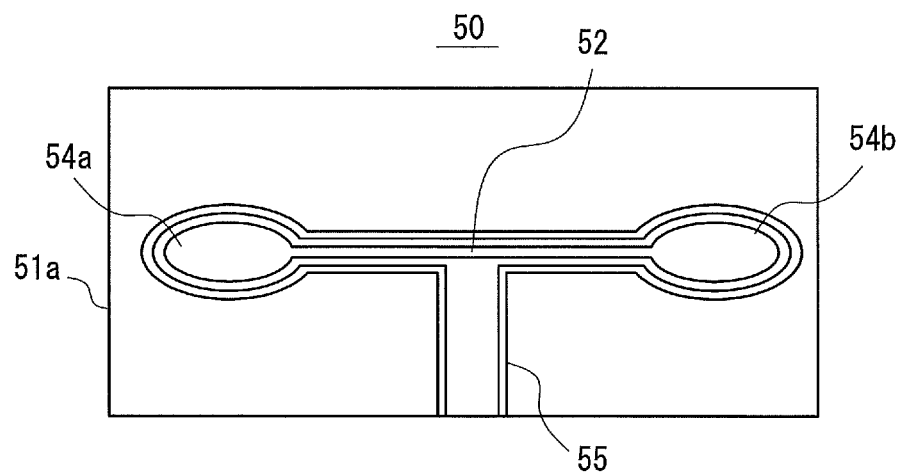

In the example shown in FIGS. 18A to 18C, a microchip 37 also includes a heat radiation member 38 in addition to the substrate 31a and the cover member 31b that covers the substrate 31a, as in the example shown in FIGS. 17A to 17C. It is, however, to be noted that in the example in FIGS. 18A to 18C, the heat radiation member 38 has a plurality of fins 39 on the bottom surface side as shown in FIGS. 18B and 18C, and therefore has improved heat radiation capability. The microchip 37 shown in FIGS. 18A to 18C is useful in the case of using an air blowing apparatus as the cooling unit in place of the electron cooling element 12.

Furthermore, in the example shown in FIGS. 19A and 19B, a microchip 50 includes a substrate 51a and a cover member 51b that covers the substrate 51a. Among these, the cover member 51b is the same as the cover member 31b shown in FIG. 2, and is provided with through holes 53a and 53b.

On the other hand, like the substrate 31a shown in FIG. 2, the substrate 51a includes a groove 52 that forms a channel, and recessed portions 54a and 54b serving as liquid reservoirs, and in addition to these constituent elements, further includes an outer groove 55. The outer groove 55 is formed along the groove 52 and the recessed portions 54a and 54b so as to surround them. When the substrate 51a and the cover member 51b are overlaid on each other, the upper surface of the outer groove 55 is blocked up. The outer groove 55 thus forms another channel like the groove 52.

As described above, in the example shown in FIGS. 19A and 19B, another channel is provided by the outer groove 55 so as to surround the vicinity of the other channel that is filled with the buffer solution. This enables the microchip 50 to be cooled by passing a cooling medium such as a liquid coolant through this channel. Furthermore, in the case of using the microchip 50 shown in FIGS. 19A and 19B, a pump that supplies a cooling medium is used as the cooling unit, in place of the electron cooling element 12.

Modification 3

Figure 20:
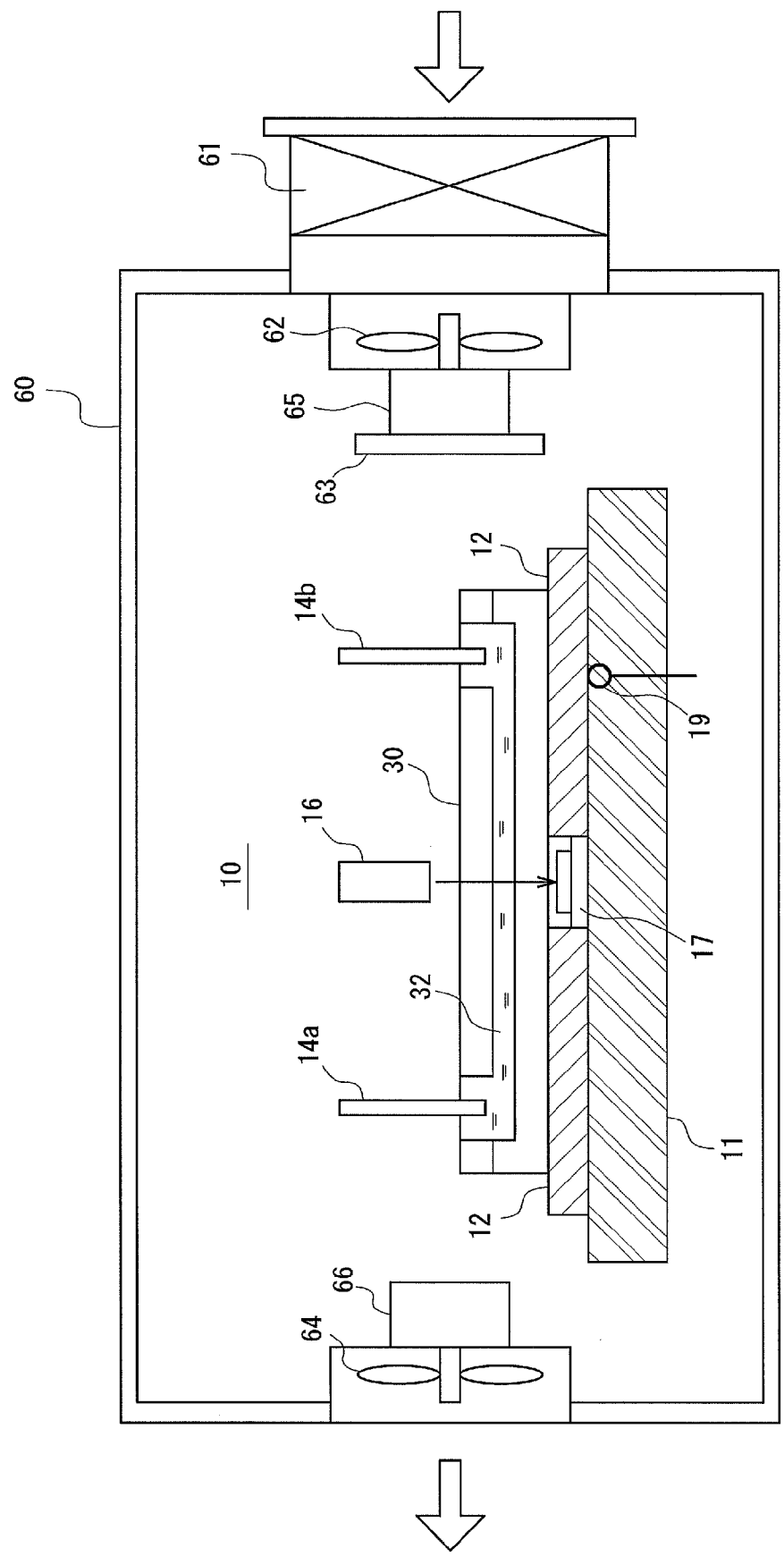
FIG. 20 shows the configuration of an analysis apparatus according to Modification 3.

Modification 3 that can be made to Embodiments 1 to 2 is described with reference to FIG. 20. FIG. 20 shows the configuration of an analysis apparatus according to Modification 3.

In Modification 3 shown in FIG. 20, the analysis apparatus 10 shown in FIG. 1 is disposed in a room 60 provided with an air circulation system. The air circulation system includes a dust-resistant filter 61, an antistatic blower 62, and a humidification filter 63 on the air intake side and includes an exhaust fan 64 on the air exhaust side. Note that reference numerals 65 and 66 in FIG. 20 denote ducts.

With this configuration, the air reaches the microchip 30 through the dust-resistant filter 61, the antistatic blower 62, and the humidification filter 63. Accordingly, Modification 3 greatly reduces the contamination of dust or the like into the microchip 30. As a result, the accuracy of the measurement can be further improved.

As described above, according to the present invention, the temperature of the microchip can be optimized in electrophoresis using a microchip. The present invention is thus useful in an electrophoresis apparatus employing a microchip.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. An electrophoresis analysis apparatus comprising:
    a microchip comprising a channel;
    a first stage configured to hold the microchip and a second stage configured to hold the microchip thereafter,
    a cooling unit configured to cool the microchip;
    wherein the cooling unit includes a first cooling unit located on the first stage configured to cool the microchip when placed on the first stage, and a second cooling unit located on the second stage configured to cool the microchip when thereafter placed on the second stage,
    a voltage application unit configured to apply a voltage to a buffer solution filled in the channel of the microchip on the second stage;
    an optical analysis unit configured to apply, through the microchip, an optical analysis of a sample introduced in the channel on the second stage;
    a control unit configured to control the cooling unit, the voltage application unit and the optical analysis unit; and
    wherein, the control unit is configured, when the microchip is placed on the first stage, to cool the microchip with the first cooling unit, and when the microchip is thereafter placed on the second stage, the control unit is configured to cause the second cooling unit increase output immediately before executing a voltage application by the voltage application unit and optical analysis by the optical analysis unit while cooling the microchip with the second cooling unit and to reduce output of the second cooling unit after operations of the voltage application unit and optical analysis unit have ended.

2. The analysis apparatus according to claim 1, wherein the control unit causes the voltage application unit and the optical analysis unit to operate, after a set period of time has elapsed since the cooling unit was caused to start cooling the microchip.

3. The analysis apparatus according to claim 1, further comprising:
    a temperature sensor for measuring a temperature of the microchip,
    wherein if the temperature measured by the temperature sensor is less than or equal to a first set temperature, the control unit causes the voltage application unit and the optical analysis unit to operate.

4. The analysis apparatus according to claim 3, wherein if the temperature measured by the temperature sensor is less than or equal to a second set temperature, the control unit causes the cooling unit to stop cooling or reduce output.

5. The analysis apparatus according to claim 1, wherein the cooling unit is at least one of an air blowing device, an electron cooling element, and a heat pipe.

6. The analysis apparatus according to claim 1, wherein
    the microchip includes a main body portion in which the channel is formed, and a heat radiation member provided on a surface of the main body portion, and
    the heat radiation member is formed from a material having higher thermal conductivity than a material forming the main body portion.

7. The analysis apparatus according to claim 1, wherein
    the microchip includes a main body portion in which the channel is formed, and
    a second channel for passing a cooling medium is further formed along the channel within the main body portion.

8. A method for performing an analysis of a sample through electrophoresis comprising:
    using the electrophoresis analysis apparatus of claim 1,
    (a) cooling the microchip on the second stage using the cooling unit; and
    (b) causing the voltage application unit and the optical analysis unit to operate, after the microchip has been cooled;
    wherein in the step (a), output of the cooling unit is increased immediately before the voltage application unit and the optical analysis unit are caused to operate, and in the step (b), the output of the cooling unit is reduced after operations of the voltage application unit and the optical analysis unit have ended.

9. The analysis method according to claim 8, wherein in the step (b), the voltage application unit and the optical analysis unit are caused to operate after a set period of time has elapsed since the cooling unit was caused to start cooling the microchip.

10. The analysis method according to claim 8, wherein
   a temperature sensor for measuring a temperature of the microchip is used, and
   in the step (b), if the temperature measured by the temperature sensor is less than or equal to a first set temperature, the voltage application unit and the optical analysis unit are caused to operate.

11. The analysis method according to claim 10, further comprising the step of:
   (c) if the temperature measured by the temperature sensor is less than or equal to a second set temperature, stopping the cooling unit from cooling the microchip or reducing output of the cooling unit.

\* \* \* \* \*